Figure 1:
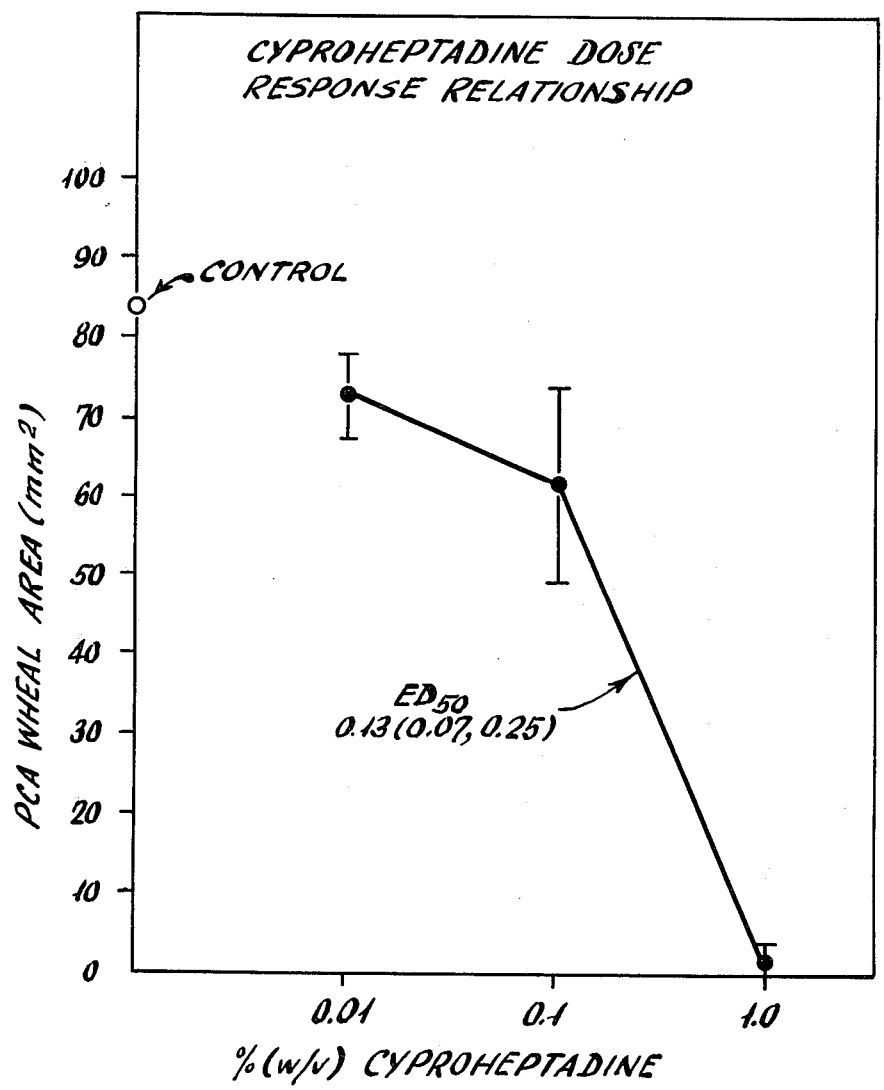

United States Patent [19]

Capetola et al.

[11] 4,444,780

[45] Apr. 24, 1984

[54] METHOD FOR TREATING ATOPIC DERMATITIS

[75] Inventors: Robert J. Capetola, Doylestown, Pa.; Marvin E. Rosenthale, Princeton, N.J.

[73] Assignee: Ortho Pharmaceutical Corporation, Raritan, N.J.

[21] Appl. No.: 412,670

[22] Filed: Aug. 30, 1982

[51] Int. Cl.$^3$ ............................................. A61K 31/445
[52] U.S. Cl. ..................................................... 424/267
[58] Field of Search ......................................... 424/267

[56] References Cited

U.S. PATENT DOCUMENTS 3,894,151 7/1975 Black et al. ........................ 424/246
4,234,566 11/1980 Packman et al. ..................... 424/47

OTHER PUBLICATIONS

Handbook of Non Prescription Drugs, 5th ed., 1977, pp. 343–349.

*Primary Examiner*—Leonard S. Henkman
*Attorney, Agent, or Firm*—Benjamin F. Lambert

[57] ABSTRACT

A method for treating atopic dermatitis with cyproheptadine or its acid addition salt is described.

6 Claims, 3 Drawing Figures

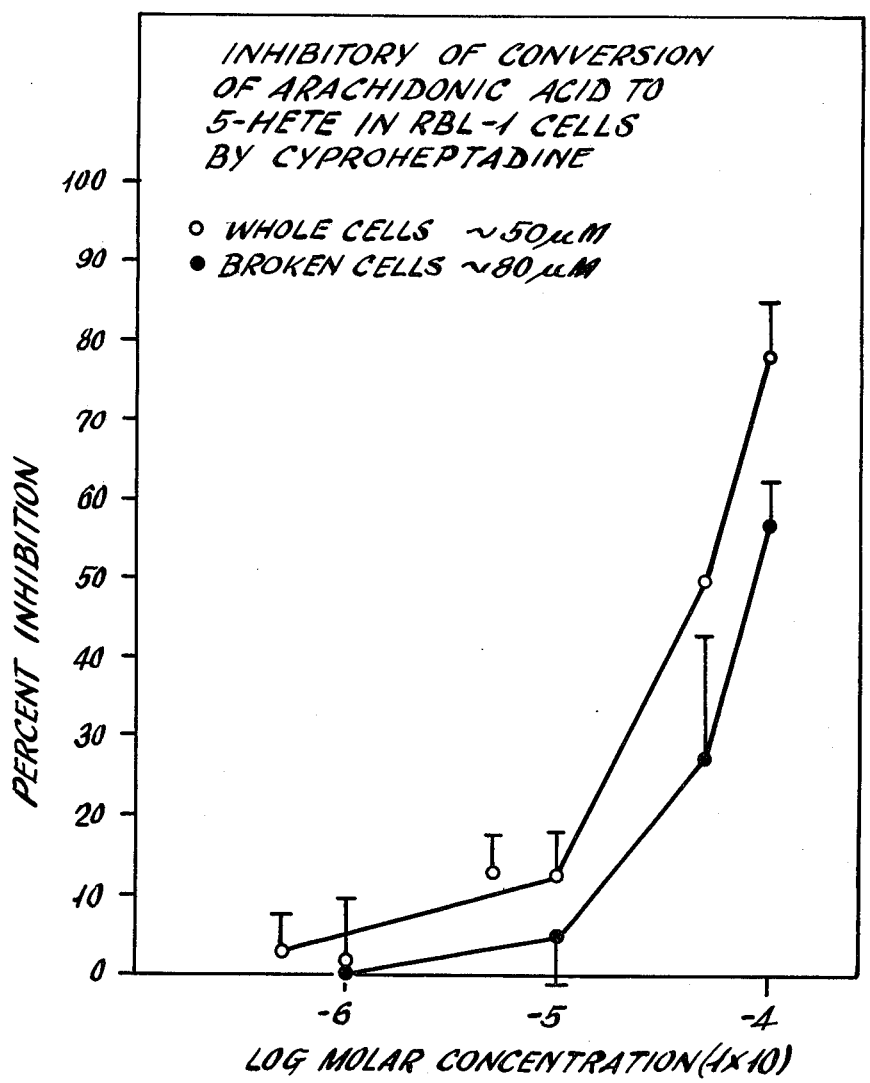

METHOD FOR TREATING ATOPIC DERMATITIS

This invention relates to a new therapeutic method for the treatment of atopic dermatitis. In particular it relates to a method for treating atopic dermatitis by the topical administration of cyproheptadine, a non-steroidal antihistaminic compound.

Eczematous and immunologic skin diseases are among the most common of all clinical afflictions. They constitute a great physical and economic impact on society and at times these conditions can be devastating to the afflicted individual. Among all dermatological diseases, atopic dermatitis is one of the most common with a prevalence between 2% and 3% in children 1-5 years old and 0.7% for all ages. Approximately 120,000-150,000 new cases of atopic dermatitis occur each year in the United States. More importantly the only effective medications that offer at least partial control of the disease are the steroids. However, widespread use of steroids can lead to skin atrophy. It has been found that cyproheptadine uniquely interrupts the most important pathophysiological events that occur in atopic dermatitis and thus offers a novel and rational approach to the treatment of atopic dermatitis.

Atopic dermatitis is a chronic disorder that can be thought of as the cutaneous manifestation of the atopic state. Atopy is a generalized term used to describe hypersensitivity diseases such as asthma, eczematous dermatitis and allergic rhinitis. Atopic persons have certain immunologic abnormalities similar to asthmatics. For example, elevated IgE levels are found in most patients with atopic dermatitis and the highest levels have been found in those patients with atopic dermatitis coexisting with allergic respiratory disease. Also patients with atopic dermatitis have elevated numbers of skin mast cells and most of the biochemical events leading to mediator release from IgE-sensitized mast cells are identical to the events occurring in the lung. Although the specific antigen necessary for bridging and activating receptive IgE antibodies on the surface of mast cells is not known, the mediators released are responsible for many of the signs and symptoms in atopic dermatitis. The major mediators released are histamine, which causes pruritus, vascular leakage leading to edema and smooth muscle contractions and products of the lipoxygenase pathway such as leukotriene B which specifically attracts inflammatory cells to the injured site and the leukotrienes C and D which can also cause smooth muscle contraction as well as increase vascular permeability. Patients with atopic dermatitis have a lowered threshhold to itch stimuli such as histamine, they have a tendency for vasoconstriction and, as previously mentioned, the disease is a chronic cutaneous inflammatory disorder which propagates the above symptoms. Thus an ideal agent for the treatment of atopic dermatitis would: (1) Be an effective antagonist of skin anaphylactic reactions, such as the passive cutaneous anaphylaxis reaction in rats; (2) Block the action of histamine at the receptor level thus relieving the itch stimuli that can lead to scratching and subsequent infection; (3) Block calcium-mediated excitation-contraction coupling on the vasculature which would relieve the vasoconstrictor tendency in atopic patients; and (4) Inhibit the lipoxygenase enzyme and thus prevent the increases in vascular permeability induced by the leukotrienes C and D as well as attenuate the influx of inflammatory cells induced by the chemoattractant, leukotriene B. The methods used to describe the unique topical antiallergic profile of cyproheptadine and the results obtained are described below.

Passive Cutaneous Anaphylaxis Test (PCA)

The PCA assay, a well known model of cutaneous atopy, was used to assess the topical antiallergic activity of cyproheptadine in a variety of formulations. Male Sprague Dawley rats (175-200 grams) were sensitized intradermally with 0.1 cc of high dilution of antiovalbumin antiserum (IgE-containing) that was predetermined to cause a well circumscribed and reproducible skin wheal response. Two intradermal sensitization sites were applied to the backs of each rat. Cyproheptadine formulations as well as other drug formulations were applied to one site and the respective vehicle was applied to the other site. One hour later the rats were challenged intravenously with a solution containing 0.5% ovalbumin and 0.5% Evans blue dye in a saline vehicle. Twenty minutes later the rats were killed by carbon dioxide asphyxiation, the dorsal skin reflected and the blue wheal measured as the mean of the two largest perpendiculars. This mean was used to calculate the area of the wheal according to $[A = \pi(d/2)^2]$. The wheal area under the drug-treated site was used as an index of local topical activity and the distant site served as an index of systemic activity.

Cyproheptadine was formulated in a vehicle comprised of water (63.78% w/w), 95% alcohol (36.1% w/w) and N-decylmethylsulfoxide (0.125% w/w) and applied topically in a volume of 0.1 ml. The dose response relationship of cyproheptadine in the PCA test is shown in FIG. 1. Cyproheptadine caused a dose-related inhibition with a topical $ED_{50}$ of 0.13% (0.07, 0.25, 95% F.L.). A comparison of cyproheptadine with standard antihistamines and calcium channel blockers for topical inhibitory activity in the PCA test is presented in Table 1. As can be seen from this Table, as well as FIG. 1, cyproheptadine caused a dose-related inhibition of this cutaneous allergic reaction with virtually complete inhibition at the 1% dose. Surprisingly, all of the classical antihistamines (hydroxyzine, chlorpheniramine, methapyrilene, phenyltoloxamine, and diphenhydramine) were inactive in this assay.

TABLE 1

Comparison of Cyproheptadine with Standard Antihistamines and Calcium Channel Blockers for Topical Antiallergic Activity in the PCA Test

| Compound | Topical Dose (%) | Percent Inhibition | Significance (P <.05) |
| --- | --- | --- | --- |
| Cyproheptadine | 0.01 | 11.7 | No |
|  | 0.10 | 25.0 | Yes |
|  | 1.00 | 98.1 | Yes |
| Hydroxyzine | 0.01 | 0 | No |
|  | 0.10 | 9.7 | No |
|  | 1.00 | 0 | No |
| Chlorpheniramine | 0.02 | 20.0 | No |
|  | 0.20 | 16.3 | No |
|  | 2.00 | 16.7 | No |
| Methapyrilene | 0.02 | 8.9 | No |
|  | 0.20 | 8.8 | No |
|  | 2.00 | 37.4 | No |
| Phenyltoloxamine | 0.02 | 2.6 | No |
|  | 0.20 | 14.3 | No |
|  | 2.00 | 25.9 | No |
| Diphenhydramine | 0.02 | 0 | No |
|  | 0.20 | 8.5 | No |
|  | 2.00 | 43.9 | No |
| Ziradryl ® (contains 2% diphenhydramine) | 2.00 | 19.3 | No |

TABLE 1-continued

Comparison of Cyproheptadine with Standard
Antihistamines and Calcium Channel Blockers for Topical
Antiallergic Activity in the PCA Test

| Compound | Topical Dose (%) | Percent Inhibition | Significance (P <.05) |
|---|---|---|---|
| Caladryl ® (contains 1% diphenhydramine) | 1.0 | 16.1 | No |
| Benadryl ® Cream (contains 2% diphenhydramine) | 2.0 | 0 | No |
| Flunarizine | 0.02 | 16.3 | No |
|  | 0.20 | 13.0 | No |
|  | 2.00 | 17.2 | No |
| Verapamil | 1% | 0 | No |

Ziradryl ® - a zinc oxide - Benadryl ® lotion
Caladryl ® - a calamine - Benadryl ® lotion
Benadryl ® Cream - diphenhydramine hydrochloride
(All commercial preparations of Parke-Davis)

Equally surprising were the data that show the commercial topical formulations, containing 1% or 2% diphenhydramine, (Ziradryl ®, Caladryl ® and Benadryl ® cream) to be inactive. Additionally, the vascular calcium channel blockers, flunarizine and verapamil, were also inactive in preventing this topical allergic reaction. These data clearly indicate the unique activity of topically administered cyproheptadine in the passive cutaneous anaphylaxis test, an activity not shared by classical antihistamines or calcium channel blockers. Thus, in addition to its well known antihistaminic and antiserotonergic properties, cyproheptadine exhibits a topical pharmacological profile distinct from other members of this therapeutic classification.

The effects of cyproheptadine for activity against two other major pathophysiological events observed in atopic dermatitis, namely, the tendency for vasoconstriction and for inhibition of chemotactic leukotrienes generated from the lipoxygenase pathway were evaluated.

Two assays were used to assess the ability of cyproheptadine to inhibit $Ca^{++}$ medicated vasoconstriction, namely $K^+$-stimulated $Ca^{++}$ uptake in aortic slices and $K^+$-stimulated $Ca^{++}$-mediated contraction of aortic strips.

Calcium Uptake in Rabbit Aorta

Female, New Zealand white rabbits (1-2 kg) were sacrificed by cervical dislocation, and the thoracic artery was immediately removed, cleaned, and sliced into rings (5-20 mg). The tissue was preincubated at 37° C. for 60 minutes. The aorta was then incubated with cyproheptadine for 10 minutes and calcium uptake was then initiated by placing the tissue into a $^{45}Ca$ buffer containing 120 mM KCl to stimulate calcium influx. After allowing radioactive calcium uptake to occur for 45 minutes, the reaction was stopped by transferring the tissue to a wash-out solution containing 80 mM $LaCl_3$ for 30 minutes. The tissue was removed, blotted of excess moisture, and weighed. The aortic slices were then placed into scintillation vials containing 1 ml Protosol tissue solubilizer and incubated overnight at 55° C. After coding and acidifying, the samples were counted to determine $^{45}Ca$ uptake.

Sample results were normalized to counts per minutes per mg, wet tissue weight. These data were calculated as ng $^{45}Ca$ uptake per mg wet tissue weight.

Potassium-Induced Calcium-Mediated Contraction of Aortic Strips

New Zealand strain rabbits (1-1.5 kg) were sacrificed by cervical dislocation and the thoracic cavity was opened to expose a section of the aorta. A section of the aorta from the diaphragm to the aortic arch was isolated, dissected out and immediately placed in chilled Krebs bicarbonate buffer solution. A 2 inch section of the aorta was supported on a glass rod in a petri dish with chilled Krebs bicarbonate solution and cleaned of excess tissue. The aorta was then cut into helical strips (3×30 mm) and suspended from a FT03 isometric force displacement transducer coupled to a Beckman recorder. The tissue bath was filled with Krebs bicarbonate buffer maintained at 37° C. and bubbled with 95% $O_2$ and 5% $CO_2$. The helical strips were allowed to equilibrate for 1.5 to 2 hours with a 4 gram resting load. The tissues were dosed in a cumulative manner with 10 mM, 15 mM, 20 mM, 30 mM, 40 mM, 80 mM and 120 mM KCl. The tissues were washed several times after the KCl treatment and were allowed to equilibrate for 1-1.5 hours until a baseline equivalent to 4 grams tension was achieved. A second dose-response to KCl was repeated and again washed and allowed to equilibrate. Cyproheptadine was then added to the bath for a period of 15-20 minutes and the KCl dose response was repeated. Changes in grams tension were recorded.

Figure 2:
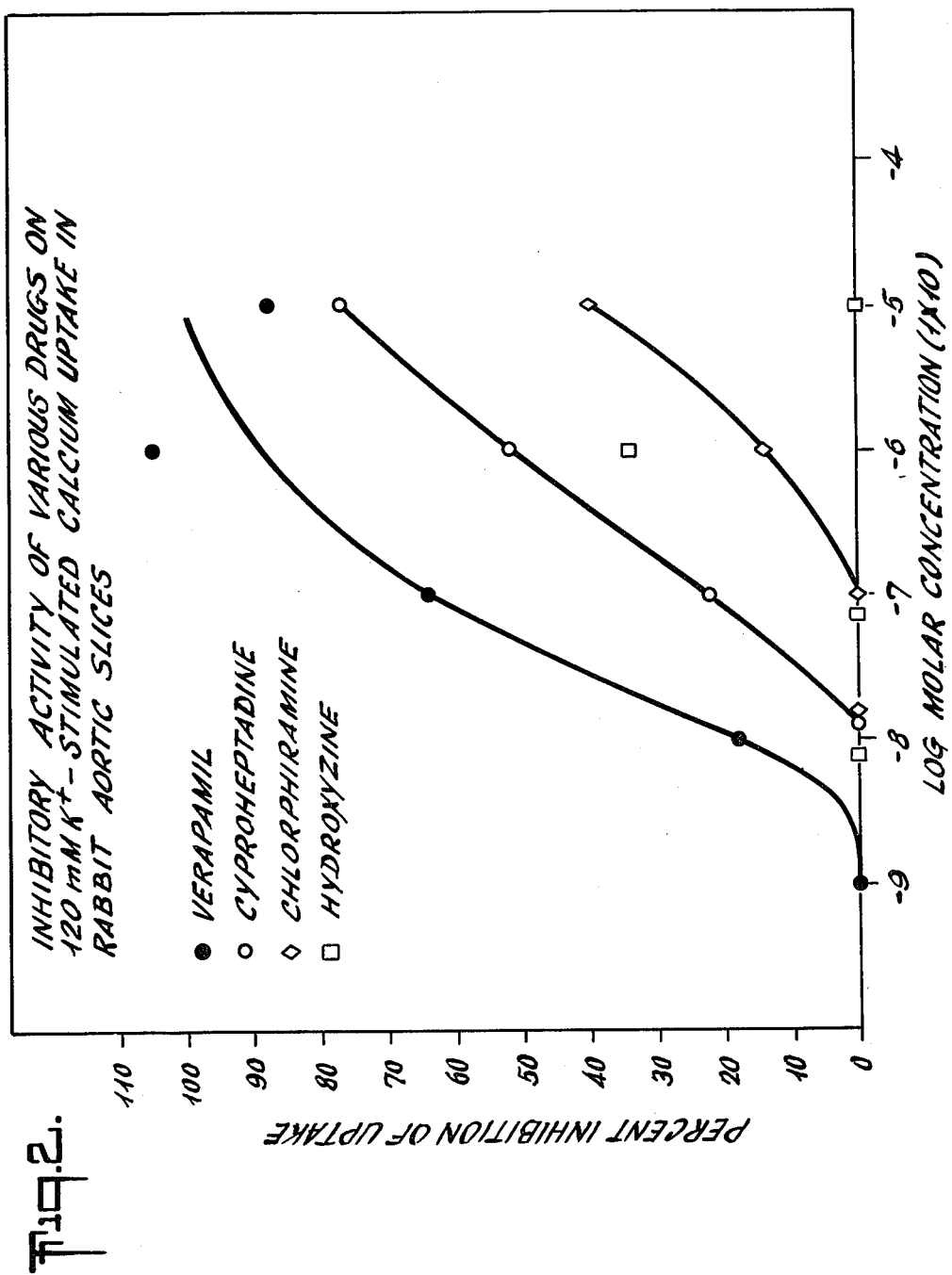

FIG. 2 shows the effects of cyproheptadine, the antihistamines chlorpheniramine and hydroxyzine and the calcium channel blocker, verapamil, on $K^+$-stimulated $Ca^{++}$-uptake in rabbit aortic slices. Verapamil caused a dose-related inhibition with an $IC_{50}$ (inhibitory concentration producing 50% inhibition) of approximately 0.1 $\mu M$. Surprisingly, cyproheptadine was also shown to be a potent inhibitor with an $IC_{50}$ of approximately 1 $\mu M$. Hydroxyzine did not produce 50% inhibition even at a concentration of an order of magnitude greater than the $IC_{50}$ for cyproheptadine. Chlorpheniramine was totally inactive. Similar results were obtained when cyproheptadine, verapamil and hydroxyzine were evaluated for activity on $K^+$-stimulated $Ca^{++}$-mediated contractions of rabbit aortic strips, as shown in Table 2. Both verapamil and cyproheptadine proved to be potent inhibitors of this vascular contraction while hydroxyzine proved to be orders of magnitude less potent.

TABLE 2

$IC_{50}$'s of Verapamil, Cyproheptadine and Hydroxyzine on $K^+$-Stimulated $Ca^{++}$-mediated Contractions of Rabbit Aortic Strips

| Compound | $IC_{50}$ ($\mu M$) |
|---|---|
| Verapamil | 0.55 |
| Cyproheptadine | 3.00 |
| Hydroxyzine | 50 |

The Effect of Cyproheptadine on Lipoxygenase in Rat Basophilic Leukemia Cells

Rat basophilic leukemia cells (RBL-1) are basophilic members of the leukocyte series and constitute a circulating form of the mast cell, i.e. they share many or all of the biochemical features of the mast cell involved in mediator release. As leukemic cells they are readily available as they can be grown in culture. RBL-1 cells were grown in minimal essential medium (MEM) containing 10% fetal calf serum, 5% calf serum, 2 mM glutamine, and 50 $\mu g/ml$ gentamicin. The cells were harvested for each assay, washed once with 50 mM potassium phosphate, 1 mM EDTA, and 0.1% gelatin, pH=7.0. The cells were then resuspended to a concentration of $1.85 \times 10^7$ cells/ml. For broken cell assays (i.e. to measure direct effects on the enzyme), these cells were sonicated in an ultrasonic sonifier for 3 minutes while maintaining the sample temperature at 4° C. Crude cell extract was used as the source of the $\Delta_5$-lipoxygenase enzyme. For the assay, $1.5 \times 10^{-6}$ cells or an equivalent amount of crude extract was incubated in the presence of $10^{-6}$ to $10^{-4}$ M cyproheptadine or vehicle (0.2% ethanol) and 2 mM $CaCl_2$ at 4° C. for 10 minutes. $^3H$-arachidonic acid (approximately 300,000 cpm) and 55 mM arachidonic acid were then added and the tubes were incubated for 10 minutes in a skaking water bath at 37° C. The reaction was stopped by the addition of 1 M citric acid to give a final pH of approximately 3.5. The reaction mixture was extracted with diethylether, brought to dryness under a stream of nitrogen and the residues were resuspended and spotted on Gilman ITLC silica gel-impregnated glass filter strips. Synthetic hydroxyeicosotetraenoic acid (5-HETE) standard was spotted with each sample and the sheets were developed in isoctane:2-butanone:glacial acetic acid (100:9:1). After development, the sheets were dried, and the 5-HETE standard was visualized in a tank of iodine crystals. Areas corresponding to 5-HETE were quantitated by liquid scintillation counting. The remainder of each lane was also counted in four sections. Activity was determined as the percent conversion of the total counts in each lane to the area corresponding to 5-HETE. Percent inhibition was calculated from the change in percent conversion in the presence of drug. Blanks determined in the presence of boiled cells were subtracted from all values.

The effect of cyproheptadine on lipoxygenase activity on whole or broken rat basophilic cells is shown in FIG. 3. Cyproheptadine caused statistically equipotent effects on lipoxygenase activity from either whole or broken cells, thus indicating a direct effect on the enzyme. Table 3 shows the effect of other antihistamines (hydroxyzine and chlorpheniramine), an antiserotonergic drug (methysergide) and a calcium channel blocker (verapamil) on lipoxygenase activity in rat basophilic cells. None of the compounds produced significant inhibition with the exception of the very high dose ($1 \times 10^{-4}$ M) of verapamil. Thus, among some standard antihistaminic and antiserotonergic compounds, cyproheptadine possesses the unique ability to selectively inhibit the generation of chemotactic leukotrienes as a result of a direct inhibitory action on the lipoxygenase pathway of arachidonic acid metabolism.

TABLE 3

Effect of Cyproheptadine, Hydroxyzine, Chlorpheniramine, Methysergide and Verapamil on Lipoxygenase Activity in Rat Basophilic Leukemia Cells

| Compound | Concentration ($\mu$M) | % Inhibition |
|---|---|---|
| Cyproheptadine | 100 | 78 |
| Hydroxyzine | 1 | 0 |
|  | 100 | 15 |
| Chlorpheniramine | 1 | 0 |
|  | 100 | 1 |
| Methysergide | 1 | 1 |
|  | 100 | 30 |
| Verapamil | 1 | 0 |
|  | 100 | 51 |

Table 4 summarizes the unique pharmacological profile of cyproheptadine, two known antihistamines and a calcium channel blocker on four pathophysiological correlates of atopic dermatitis.

TABLE 4

| Drug | Topical PCA Activity | Inhibition of $^{45}Ca^{++}$-Uptake Aortic Slices | Inhibition of $Ca^{++}$ Contraction Vascular Tissue | Inhibition of Lipoxygenase |
|---|---|---|---|---|
| Cyproheptadine | +++ | ++ | ++ | +++ |
| Chlorpheniramine | − | + | − | − |
| Hydroxyzine | − | − | + | − |
| Verapamil | − | +++ | +++ | + |

Only cyproheptadine possesses the ability to attenuate all of these mechanisms in conjunction with a potent topical antiallergic effect on the PCA reaction. The standard antihistamines, chlorpheniramine and hydroxyzine, had marginal effects on calcium mechanisms but were totally inactive topically in the PCA and lipoxygenase assays. Likewise, verapamil, a standard calcium channel blocker, exhibited potent effects on the calcium movement assays and had slight activity on the lipoxygenase assay, but most importantly was totally inactive in the cutaneous anaphylaxis assay (PCA) in vivo.

As indicated above, cyproheptadine is a potent antihistamine. When administered orally at high dosage levels, cyproheptadine can be used to treat pruritis, however, due to the high dosage level required, such use is generally associated with side effects which affect the central nervous system. Topical administration of cyproheptadine allows for the treatment of pruritis at the source of the itch without the side effects associated with oral administration of the compound.

Cyproheptadine can be administered topically in a pharmaceutically acceptable carrier in the form of a cream, ointment, lotion or gel, for example. Generally concentrations ranging from about 0.05-3% by weight of the compound are employed. The preferred dosage range is about 0.5 to 2%. The compound can be employed either as the free base or as an acid addition salt such as the hydrochloride or hydrobromide.

The following examples are provided by way of illustration and are not intended to limit the scope of the present invention, the scope of which is defined by the appended claims.

Example 1

| Shampoo | % w/w |
|---|---|
| Cyproheptadine Hydrochloride | 1.0 |
| Amphoteric 10 | 20.0 |
| Sodium Lauryl Sulfate (28%) | 10.0 |
| Sodium Lauryl Ether Sulfate (23%) | 10.0 |
| Lauric Diethanolamide | 1.0 |
| Polysorbate 20 | 1.0 |
| Hexylene Glycol | 2.0 |
| Benzyl Alcohol | 1.0 |
| Purified Water to make | 100.0 |

Example 2

| Cream | % w/w |
|---|---|
| Cyproheptadine Hydrochloride | 1.0 |
| Polyoxyl 40 Stearate | 5.0 |

-continued

| Cream | % w/w |
| --- | --- |
| Cetostearyl Alcohol | 6.0 |
| White Petrolatum | 5.0 |
| Mineral Oil | 5.0 |
| Xanthum Gum | 0.3 |
| Sorbitan Monostearate | 0.2 |
| Benzoic Acid | 0.2 |
| Purified Water to make | 100.0 |

Example 3

| Ointment | % w/w |
| --- | --- |
| Cyproheptadine Hydrochloride | 1.0 |
| Stearyl Alcohol | 25.0 |
| Petrolatum | 25.0 |
| Propylene Glycol | 12.0 |
| Sodium Lauryl Sulfate | 1.0 |
| Methyl Paraben | 0.025 |
| Propyl Paraben | 0.015 |
| Purified Water to make | 100.00 |

Example 4

| Solution | % w/w |
| --- | --- |
| Cyproheptadine Hydrochloride | 1.0 |
| Ethyl Alcohol | 36.1 |
| Purified Water to make | 100.0 |

Example 5

| Solution With Skin Penetration Enhancer | % w/w |
| --- | --- |
| Cyproheptadine Hydrochloride | 1.0 |
| N—Decyl Methyl Sulfoxide | 0.125 |
| Ethyl Alcohol | 36.1 |
| Purified Water to make | 100.0 |

Example 6

| Alcoholic Gel | % w/w |
| --- | --- |
| Cyproheptadine Hydrochloride | 1.0 |
| Hydroxypropyl Cellulose | 3.0 |
| Ethyl Alcohol to make | 100.0 |

Example 7

| Lotion | % w/w |
| --- | --- |
| Cyproheptadine Hydrochloride | 1.0 |
| Calamine | 8.0 |
| Zinc Oxide | 8.0 |
| Glycerin | 2.0 |
| Bentonite Magma | 25.0 |
| Calcium Hydroxide Solution to make | 100.0 |

Example 8

| Lotion | % w/w |
| --- | --- |
| Cyproheptadine Hydrochloride | 1.0 |
| Mineral Oil | 30.0 |
| Sorbitan Monoleate | 1.0 |
| Polysorbate 30 | 4.0 |
| Benzoic Acid | 0.2 |
| Purified Water to make | 100.0 |

Example 9

| Aqueous Gel | % w/w |
| --- | --- |
| Poloxamer 407 | 20.0 |
| Cyproheptadine Hydrochloride | 1.0 |
| Propylene Glycol | 2.0 |
| Benzyl Alcohol | 1.0 |
| Purified Water to make | 100.0 |

What is claimed is:

1. A method of treating a subject afflicted with atopic dermatitis which comprises topically administering to said subject an effective amount of cyproheptadine or its acid addition salt in a pharmaceutically acceptable carrier.

2. The method of claim 1 wherein the cyproheptadine is present in an amount from about 0.05 to 3% by weight.

3. The method of claim 2 wherein the cyproheptadine is administered in the form of a cream.

4. The method of claim 2 wherein the cyproheptadine is administered in the form of an ointment.

5. The method of claim 2 wherein the cyproheptadine is administered in the form of a lotion.

6. The method of claim 2 wherein the cyproheptadine is administered in the form of a gel.

* * * * *